(12) United States Patent
Wilson et al.

(10) Patent No.: US 6,662,391 B2
(45) Date of Patent: Dec. 16, 2003

(54) BED LATCH POSITION DETECTOR AND METHOD

(75) Inventors: Scott K. Wilson, Stuart, FL (US); Barry Hand, Mount Pleasant, SC (US); Jack Brooks, Folly Beach, SC (US); Fred York, Longwood, FL (US); Richard Calcutta, Ormond Beach, FL (US)

(73) Assignee: Hi-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/791,936

(22) Filed: Feb. 23, 2001

(65) Prior Publication Data

US 2002/0013965 A1 Feb. 7, 2002

Related U.S. Application Data

(60) Provisional application No. 60/184,293, filed on Feb. 23, 2000.

(51) Int. Cl.⁷ .................................................. A61B 6/04
(52) U.S. Cl. ................................................. 5/600; 5/601
(58) Field of Search .............................. 5/600, 601, 607

(56) References Cited

U.S. PATENT DOCUMENTS

| | | | |
|---|---|---|---|
| 516,614 A | 3/1894 | Seaman | 5/131 |
| 795,155 A | 7/1905 | Nees | 340/545.6 |
| 2,734,104 A | 2/1956 | Gollhofer | 200/61.75 |
| 3,514,794 A | 6/1970 | Pofferi | 5/2.1 |
| 3,840,221 A | 10/1974 | Hogan | 5/601 |
| 4,017,737 A | 4/1977 | Hudson et al. | 378/39 |
| 4,231,030 A | 10/1980 | Weiss | 340/686.1 |
| 4,578,833 A * | 4/1986 | Vrzalik | 5/607 |
| 4,593,264 A | 6/1986 | Engle | 340/431 |
| 4,660,236 A | 4/1987 | Peterson | 5/618 |
| 4,672,952 A * | 6/1987 | Vrzalik | 601/90 |
| 4,811,435 A | 3/1989 | Foster et al. | 5/600 |
| 4,908,844 A * | 3/1990 | Hasegawa | 5/601 X |
| 4,951,032 A | 8/1990 | Langsam | 340/522 |
| 5,159,312 A | 10/1992 | Engle | 340/431 |
| 5,250,802 A | 10/1993 | Runner | 250/227.15 |
| 5,297,225 A * | 3/1994 | Snow et al. | 385/25 |
| 5,396,673 A | 3/1995 | Foster | 5/600 |
| 5,425,148 A | 6/1995 | Ashcraft et al. | 5/507.1 |
| 5,450,639 A * | 9/1995 | Weismiller et al. | 5/600 |
| 5,477,570 A * | 12/1995 | Hannant et al. | 5/600 X |
| 5,497,097 A | 3/1996 | Walling et al. | 324/555 |
| 5,596,779 A * | 1/1997 | Meek | 5/600 |
| 5,621,932 A * | 4/1997 | Strachan | 5/600 |
| 5,949,329 A | 9/1999 | Woodard | 340/431 |
| 6,021,533 A | 2/2000 | Ellis et al. | 5/600 |
| 6,315,740 B1 * | 11/2001 | Singh | 600/595 |
| 6,320,510 B2 * | 11/2001 | Menkedick et al. | 5/600 X |
| 2002/0013965 A1 * | 2/2002 | Wilson et al. | 5/600 |
| 2003/0037375 A1 * | 2/2003 | Riley et al. | 5/600 |

FOREIGN PATENT DOCUMENTS

EP   0 641 545 A1   9/1994

OTHER PUBLICATIONS

"Plane Surfaces and Prisms", *Fundamentals of Optics*, pp. 40–41, date unknown.

* cited by examiner

Primary Examiner—Robert G. Santos
(74) Attorney, Agent, or Firm—Bose McKinney & Evans LLP

(57) ABSTRACT

A bed is provided for supporting a patient thereon. The bed includes a first bed component that is movable relative to a second bed component. The bed further includes a position detector configured to detect the position of the second bed component relative to the first bed component.

29 Claims, 10 Drawing Sheets

US 6,662,391 B2

BED LATCH POSITION DETECTOR AND METHOD

This application claims benefit of U.S. Provisional Application Serial No. 60/184,293, filed Feb. 23, 2000, the disclosure of which is expressly incorporated by reference herein.

BACKGROUND AND SUMMARY OF THE INVENTION

The invention relates generally to beds and more particularly to hospital beds having latch sensors for determining when a latch is in a latched or unlatched position.

Caregivers often use backboards and patient shifting boards to transport patients who have suffered a spinal or neck injury from an accident scene to a care facility such as a hospital. To avoid further injury to a patient's spine or neck, the caregiver carefully straps the patient to the backboard to immobilize the patient. Once immobilized, further movement of the patient is avoided to minimize the risk of further injury. To diagnose the patient's injuries, the caregiver takes X-rays or magnetic resonance images (MRI's) of the patient. During the X-rays and MRI's, the caregiver must often rotate or move the patient to various positions. Furthermore, if the caregiver discovers a spinal or neck injury, the caregiver may need to immobilize the patient to the backboard for an extended period of time. During this time, the caregiver may administer treatment and physical therapy that often requires that the patient again be rotated or moved.

One method of rotating or moving a patient from a horizontal plane is provided by attaching the backboard to a hospital bedframe equipped with a plurality of latches that secure the backboard to the bedframe. The bedframe rotates the backboard about a horizontal axis, and may raise or lower the backboard at an angle relative to the horizontal axis. Because rapid movements or even slight, but abrupt, movements should be avoided, it is preferable that the latches securing the backboard to the bedframe be in a latched position before the bedframe undergoes any motion. Thus, the position of the latches should be determined before permitting movement of the backboard. This latch position determination aids in preventing the backboard from slipping or falling from the bedframe due to any of the latches being in the unlatched position.

According to the present invention, a position detector is provided for use with a bedframe including first and second components such as a frame member and a latch positioned to couple a backboard to the frame member. The second component is movable between first and second positions relative to the first component. The position detector includes a conductor and a sensor. The conductor has a property that changes between a first state and a second state upon movement of the second component of the bedframe from the first position to the second position. The sensor is coupled to the conductor to detect the change in state of the property of the conductor to determine the position of the second component of the bedframe based on the detected change in state of the property of the conductor.

According to a preferred embodiment of the present invention, a bed is provided. The bed includes a support surface configured to support a person, a bedframe configured to support the support surface, and a position detector. The bedframe includes a frame member and multiple components configured to move relative to the frame member between first and second positions. The position detector includes a conductor and a sensor. Each of the multiple components is positioned to communicate a change in position of said component to the conductor. The sensor is coupled to the conductor to detect the change in position of each of the multiple components to determine the positions of said components.

According to the present invention, a method of detecting a position of a first bed component relative to a second bed component is provided. The first bed component is movable between first and second positions relative to the second bed component. The method includes the steps of providing a conductor positioned to be acted upon by the first bed component; moving the first bed component from the first position to the second position; changing a property of the conductor from a first state to a second state during movement of the first bed component from the first position to the second position; detecting the state of the property of the conductor; and correlating the state of the property of the conductor with the position of the first bed component to determine the position of the first bed component.

A preferred method of detecting the position of multiple bed components movable between first and second positions relative to a bedframe is also provided. The method includes the step of providing a conductor having a region associated with each of the multiple bed components. Each region of the conductor is positioned to be manipulated by one of the multiple bed components. The method further includes the steps of moving at least one of the multiple bed components from the first position to the second position; changing a property of the region of the conductor associated with said bed component moved to the second position; detecting the state of the property of each region of the conductor; and correlating the state of the property of each region of the conductor with the position of each associated bed component to determine the position of each associated bed component.

Additional features of the disclosure will become apparent to those skilled in the art upon consideration of the following detailed description when taken in conjunction with the accompanying drawings.

DETAILED DESCRIPTION OF THE INVENTION

Figure 1:
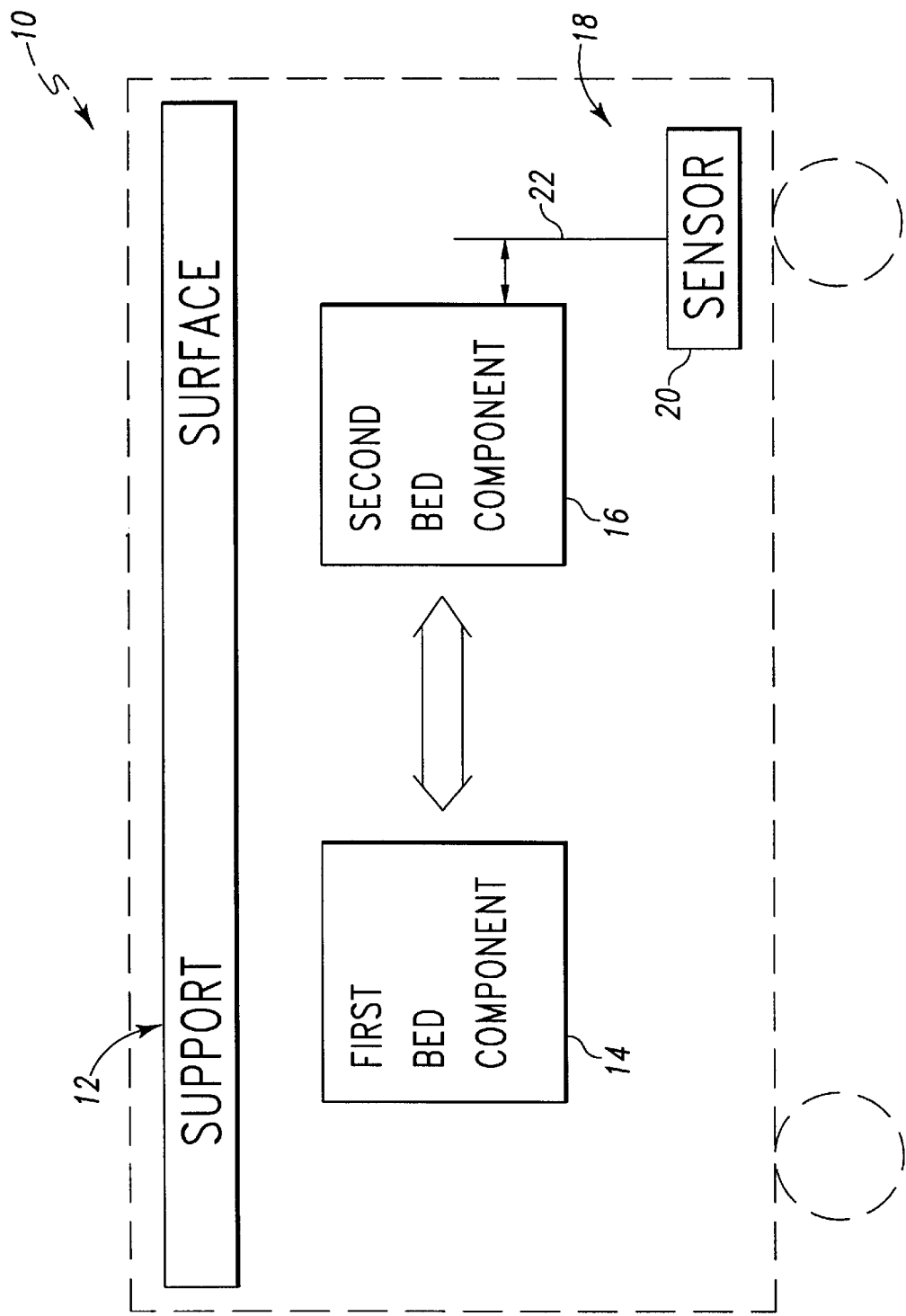
FIG. 1 is a diagrammatic view of a bed showing the bed including a support surface, first and second bed components, and a position detector including a sensor and a conductor coupled to the sensor, the second bed component being movable relative to the first bed component, and the second bed component acting upon the conductor during the movement relative to the first bed component.

As shown in FIG. 1, a bed 10 is provided for supporting a person (not shown). Bed 10 includes a support surface 12 for supporting the person, a first bed component 14, and a second bed component 16. Second bed component 16 is movable relative to first bed component 14 between first and second positions. Bed 10 further includes a position detector 18 configured to detect the position of second bed component 16 relative to first bed component 14.

Position detector 18 includes a sensor 20 and a conductor 22 as shown in FIG. 1. Second bed component 16 is positioned to act upon conductor 22 during movement between the first and second positions to change a property of conductor 22 from a first state to a second state. Sensor 20 is coupled to conductor 22 to detect the change in property of conductor 22 and to associate the change in property of conductor 22 with the change in position of second bed component 16 relative to first bed component 14 to detect the position of second bed component 16 relative to first bed component 14.

Position detector 18 is capable of detecting the position of many bed components. For example, the position of bed latches, siderails, deck panels, pedals, frame members, gates, actuators, mattress components, valves, wheels, linkages, or any other bed components may be detected using position detector 18.

Figure 2:
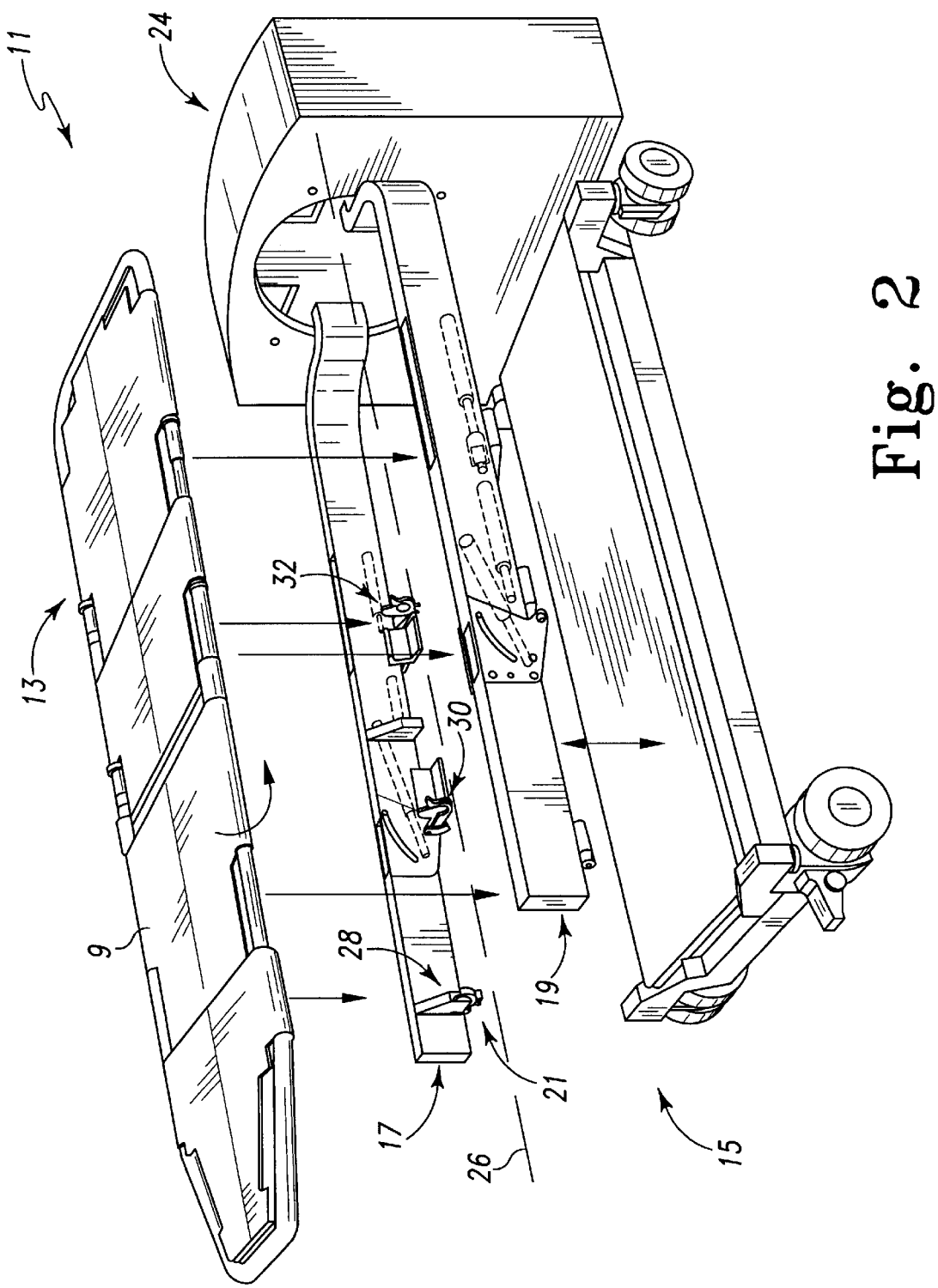
FIG. 2 is a perspective view of a preferred hospital bed showing the hospital bed including a bedframe and a removable patient backboard positioned above the bedframe to be rigidly coupled thereto and the bedframe including a pair of horizontally extending frame members and a latch system having first, second, and third latches coupled to each of the support members.

As shown in FIG. 2, a presently preferred hospital bed 11 is provided for supporting a patient during diagnosis and treatment of injuries. Hospital bed 11 includes a backboard 13 defining a support surface 9 on which a caregiver positions and immobilizes a patient for diagnosis and treatment of injuries. Hospital bed 11 further includes a bedframe 15 configured to support backboard 13 above the floor.

Bedframe 15 includes a pair of frame members 17, 19 that support backboard 13. To secure backboard 13 to frame members 17, 19, bedframe 15 further includes a latch system 21 that couples backboard 13 to frame members 17, 19. To insure that latch system 21 is properly securing backboard 13 to bedframe 15, hospital bed 11 also includes a latch position detector 23 as shown diagrammatically in FIG. 3. Latch position detector 23 is a preferred embodiment of position detector 18 that senses the position of latch system 21 to determine if and when backboard 13 is unlatched, latched, or partially latched to frame members 17, 19 by latch system 21.

To aid in diagnosis and treatment, bedframe 15 is configured to move and rotate backboard 13 between several positions. Latch position detector system 23 is configured to prevent movement of backboard 13 by bedframe 15 unless latch system 21 is properly securing backboard 13 to frame members 17, 19. Therefore, if any of the latches of latch system 21 are unlatched or only partially latched, latch position detector 23 will instruct bedframe 15 not to move backboard 13 until properly latched to bedframe 15.

As shown in FIG. 2, bedframe 15 further includes a mover 24 positioned to move and rotate backboard 13 during diagnosis and treatment. Frame members 17, 19 are coupled to mover 24. To position the patient for diagnosis or treatment, mover 24 rotates frame members 17, 19 and backboard 13 about a horizontal axis 26 of rotation. Mover 24 is configured to rotate backboard 13 up to 180 degrees about horizontal axis 26, e.g., a patient secured to backboard 13 and facing upward may be rotated 180 degrees to face downwardly. During this rotation, latch system 21 continues to secure backboard 13 to frame members 17, 19.

As shown in FIG. 2, preferred latch system 21 includes first, second, and third latches 28, 30, 32 coupled to each frame member 17, 19. Each latch 28, 30, 32 is positioned to couple to a specific portion of backboard 13 to secure backboard 13 to bedframe 15 in six locations.

Figure 3:
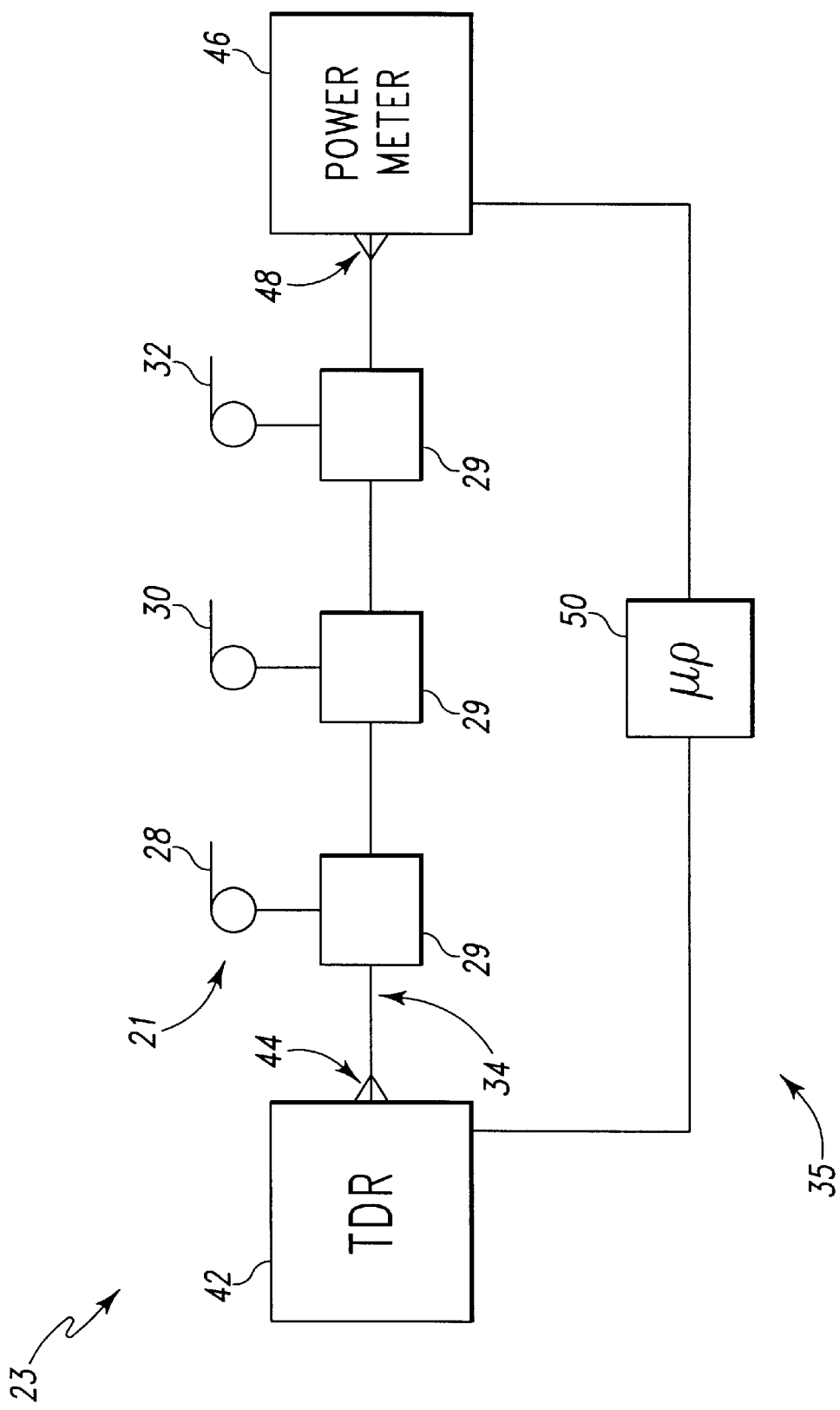
FIG. 3 is a diagrammatic view of a preferred embodiment position detector showing the position detector including a conductor and a sensor having a time domain reflectometer (TDR) coupled to a first end of the conductor, a power meter coupled to a second end of the conductor, and a microprocessor ($\mu$P) coupled to the time domain reflectometer and the power meter, the hospital bed further including three conductor manipulators positioned over three regions of the conductor to change a property of the regions of the conductor between first and second states, and the three latches positioned to act upon the regions of the conductor through the three conductor manipulators to change the state of the regions between the first and second states.

As shown diagrammatically in FIG. 3, latch position detector 23 interacts with each latch 28, 30, 32 to detect whether the respective latch 28, 30, 32 is in the latched, unlatched, partially latched, or other position. According to the preferred embodiment, latch position detector 23 includes a fiber optic cable 34 as a preferred conductor, a sensor 35, and three conductor manipulators 29 through which the associated latches 28, 30, 32 act upon fiber optic cable 34.

As shown in FIG. 3, cable 34 extends through each conductor manipulator 29 to communicate the position of respective latches 28, 30, 32 to cable 34 by acting upon regions associated with each latch 28, 30, 32. Cable 34 then communicates this position related information through cable 34 to sensor 35. Thus, each latch 28, 30, 32 acts upon cable 34 to change a property of cable 34 from a first state to a second state. This change in state is then analyzed by sensor 35 to detect the position of latches 28, 30, 32. If any of latches 28, 30, 32 are detected in the unlatched position, mover 24 is disabled.

Preferably, sensor 35 includes a time domain reflectometer (TDR) 42 coupled to cable 34 by a cable head 44 and a power meter 46 coupled to cable 34 at a cable tail 48 as shown in FIG. 3. Time domain reflectometer 42 transmits an energy pulse of light into cable 34. This light is used as a communication signal that travels through cable 34 to communicate latch position information. As the light travels through cable 34, portions of the light are reflected back to time domain reflectometer 42 by reflective regions of cable 34. Such reflective regions exist in cable 34 due to certain properties of cable 34 in the reflective regions. For example, cable head 44, cable tail 48, and manipulation created by conductor manipulators 29 create reflective regions in cable 34.

Sensor 35 further includes a microprocessor 50 coupled to time domain reflectometer 42 that is configured to interpret the reflections from cable 34. Microprocessor 50 is configured to (1) analyze the reflections created by the manipulated regions of cable 34 due to manipulations of cable 34 by conductor manipulator 29 and (2) determine the position of the associated latch 28, 30, 32 based on the reflection. Power meter 46 is also coupled to microprocessor 50 to detect whether a failure exists within cable 34.

Preferably, cable 34 runs by each latch 28, 30, 32, or other movable bed component so that only one sensor 35 is needed. However, according to alternative embodiments, multiple conductors and sensors are used for multiple movable bed components.

Figure 4:
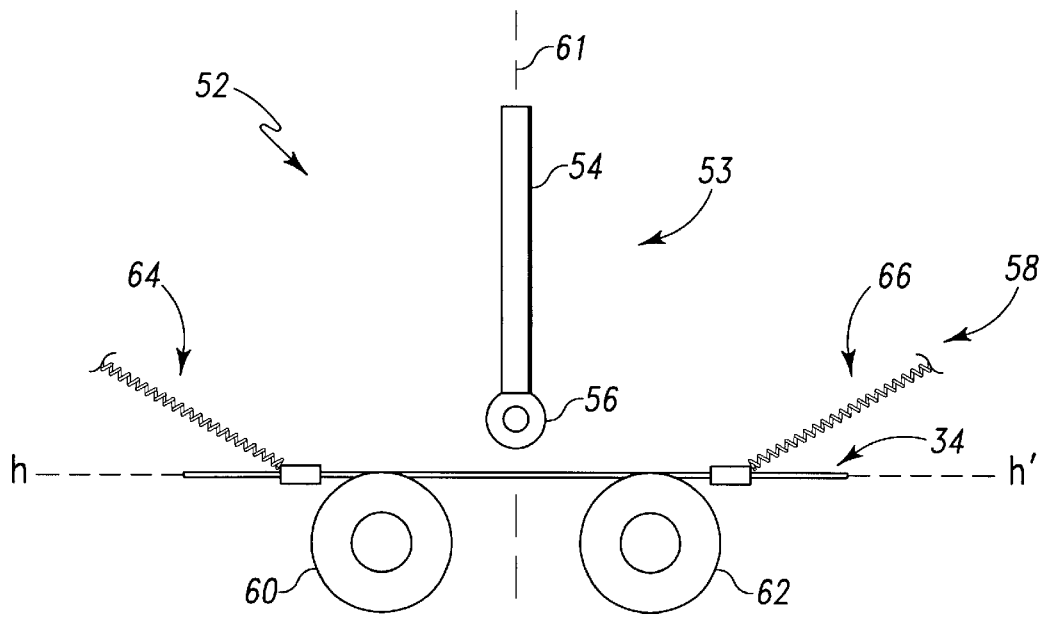
FIG. 4 is a diagrammatic view of a preferred conductor manipulator in the form of a conductor bend apparatus having a rod-shaped contact element and a pair of pulleys, the conductor lying over the pulleys, and the contact element being in a deactuated position corresponding to an associated latch in a latched position.
Figure 5:
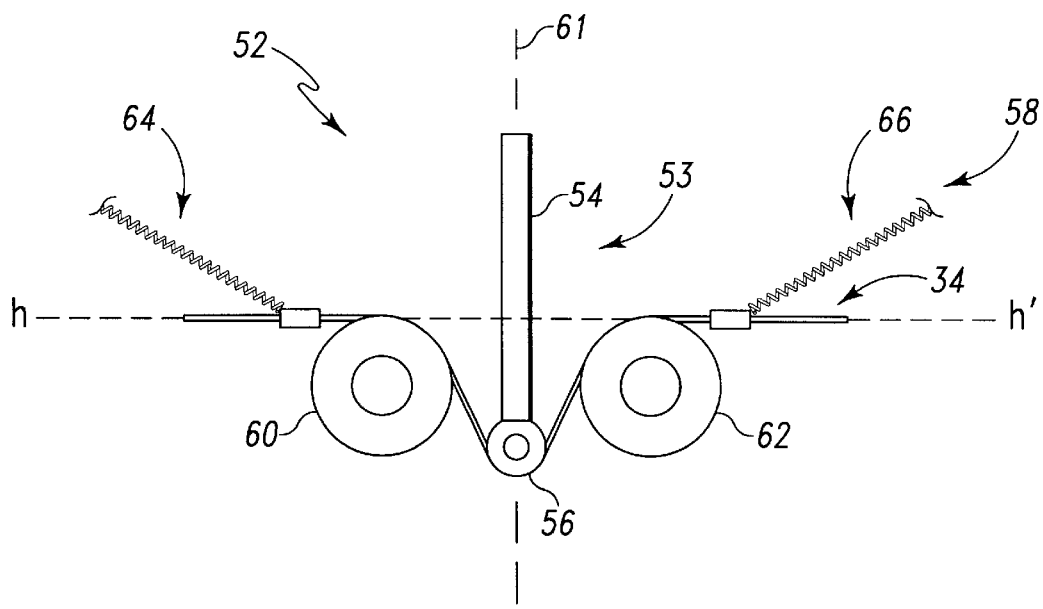
FIG. 5 is view similar to FIG. 4 showing the contact element in an actuated position bending the conductor between the pulleys when the associated latch is in an unlatched position.

A preferred conductor manipulator is shown in FIGS. 4 and 5 as conductor bend apparatus 52. Conductor bend apparatus 52 communicates the position of each latch 28, 30, 32 to cable 34 by bending a region of cable 34 to change the state of a property of cable 34. As shown in FIGS. 4 and 5, conductor bend apparatus 52 moves from a deactuated position wherein cable 34 has a generally straight shape to an actuated position wherein cable 34 has a bent shape. Conductor bend apparatus 52 is moved to the actuated position, as shown in FIG. 5, when the associated latch 28, 30, 32 is in the unlatched position and to the deactuated position, as shown in FIG. 4, when the associated latch 28, 30, 32 is in the latched position. Thus, movement of the associated latch 28, 30, 32 changes the associated region of cable 34 to a bent shape when the associated latch 28, 30, 32 is in the unlatched position and to a straight shape when the associated latch 28, 30, 32 is in the latched position.

As shown in FIG. 4, conductor bend apparatus 52 includes a contact element 53 and first and second pulleys 60, 62. Contact element 53 includes a shuttle 54 and bulb 56 coupled to an end of shuttle 54. Shuttle 54 is positioned to interact with the associated latch 28, 30, 32 so that shuttle 54 is moved relative to pulleys 60, 62 to the actuated position when the associated latch 28, 30, 32 is in the unlatched or partially latched position, as shown in FIG. 5, and in the deactuated position relative of pulleys 60, 62 when the associated latch 28, 30, 32 is in the latched position as shown in FIG. 4. Thus, shuttle 54 and bulb 56 reciprocate between the actuated and deactuated positions as the associated latch 28, 30, 32 is unlatched and latched.

Pulleys 60, 62 are proximately spaced and shuttle 54 is positioned along an axis 61 that extends between pulleys 60, 62. As shown in FIGS. 4 and 5, cable 34 is positioned between pulleys 60, 62 and shuttle 54. Thus, when contact element 53 is in the deactuated position, bulb 56 is positioned above a horizontal plane hh' common to the top of pulleys 60, 62 and cable 34 runs across the top of pulleys 60, 62 in plane hh'.

The reciprocation of bulb 56 along axis 61 moves cable 34 between the bent and unbent positions as shown in FIGS. 4 and 5 creating and removing reflective regions in cable 34. When the associated latch 28, 30, 32 is moved to the unlatched position, shuttle 54 plunges downwardly into plane hh', as shown in FIG. 5. Bulb 56 engages cable 34 in the region common to pulleys 60, 62, thereby pushing cable 34 downwardly to the bent position. Because pulleys 60, 62 are proximately spaced, cable 34 is bent to a position having a bend radius less than a predetermined bend radius. When the bend radius drops below the predetermined radius, cable 34 develops a reflective region that reflects a portion of the light pulse traveling through cable 34 back toward time domain reflectometer 42.

The predetermined bend radius is dependent on the cable type and is available from the cable manufacturer. For example, the maximum bend radius that will not create a reflective region in most fiber optic cables not in tension is 10 times the diameter of the cable. For fiber optic cables under tension, the maximum bend radius is 20 times the diameter of the cable. Thus, the predetermined bend radius for a specific cable varies by the cable type and manufacturer, and whether the cable is in tension.

When a light pulse is transmitted through cable 34 while cable 34 is bent by conductor bend apparatus 52, a reflection is created to indicate that at least one of latches 28, 30, 32 is in the unlatched position. No reflection will be created when the associated latch 28, 30, 32 is in the latched position because conductor bend apparatus 52 does not create a bend in the associated region of cable 34. The existence or absence of the reflection is detected by microprocessor 50 and correlated with the position of the associated latch 28, 30, 32.

To facilitate return of cable 34 from the bent position to the unbent position, conductor bend apparatus 52 further includes a cable return system 58 configured to bias cable 34 to the unbent position. As shown in FIG. 5, cable return system 58 includes a pair of tension springs 64, 66. Tension springs 64, 66 are coupled to cable 34 and another component of hospital bed 11 to apply a force to and bias cable 34 upwardly from the bent position into plane hh' as shown in FIG. 4.

According to alternative embodiments, the bed component directly acts upon the conductor to manipulate a property of the conductor. For example, where the bed component is a latch, the latch itself acts on the conductor. Where the siderail is the bed component being monitored, the siderail itself acts directly on the conductor. Thus, a separate conductor manipulator is not always necessary to manipulate the conductor.

During operation of latch position detector 23, time domain reflectometer 42 transmits an energy pulse in the form of a light pulse into cable 34 through cable head 44. As the energy pulse propagates through cable 34, reflections are created at regions where impedance mismatches occur and at bent cable regions. These reflections then propagate back to cable head 44 where they are received by time domain reflectometer 42. Thus, when latch 28, 30, 32 is in the unlatched position, shuttle 54 of conductor bend apparatus 52 is in the actuated position, a bent region is created in cable 34 causing a reflection of a portion of the energy pulse. Because shuttle 54 is only actuated when the associated latch 28, 30, 32 is in the unlatched position, the generation of a reflection indicates that the associated latch 28, 30, 32 is not in the latched position.

Figure 6:
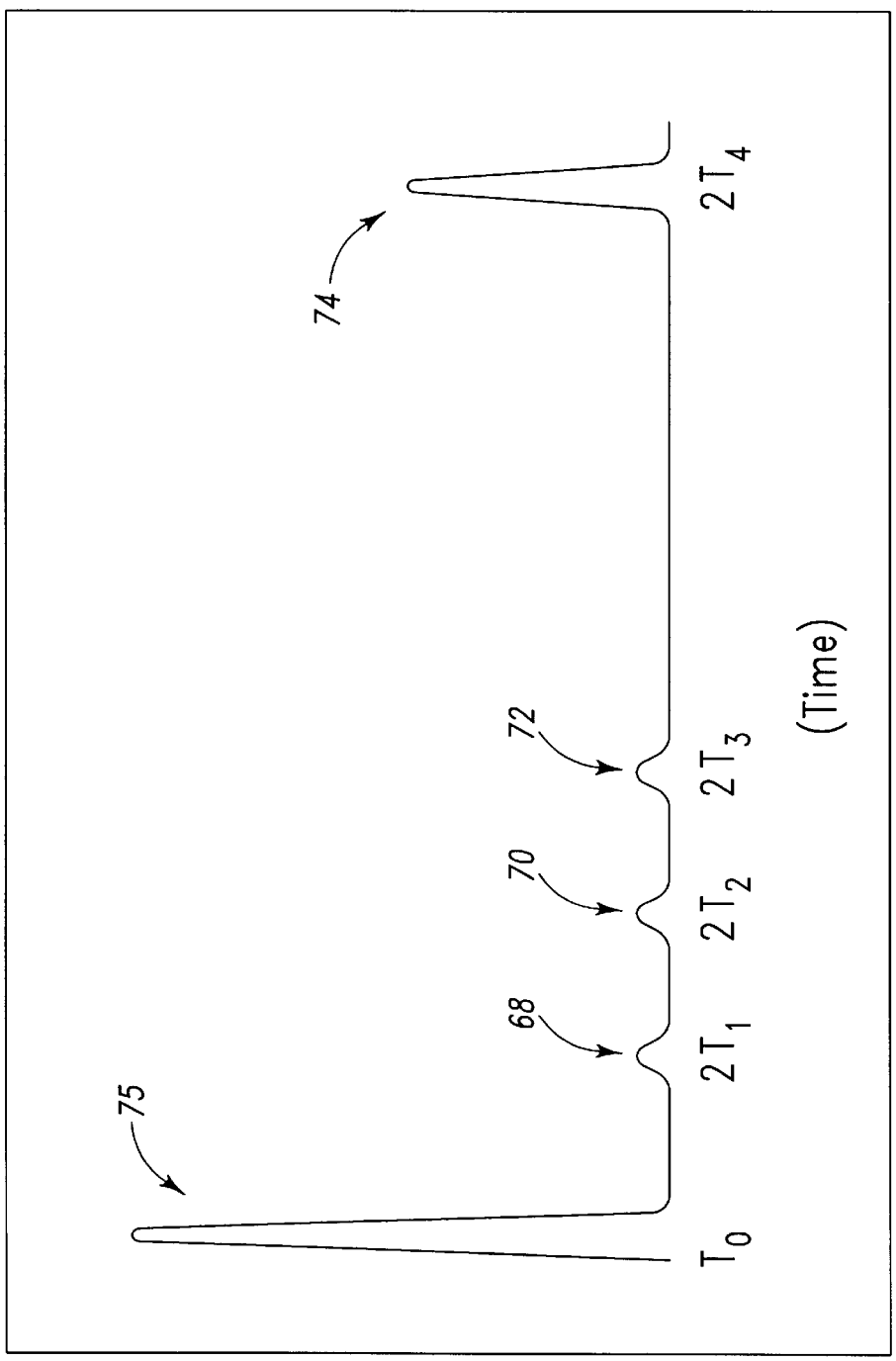
FIG. 6 is a graph showing a time domain reflectometer reading for the latch system when the first, second, and third latches are in the unlatched position generating three corresponding medium crests between two large crests which are associated with the first and second ends of the conductor.

A time domain reflectometer reading for first, second, and third latches 28, 30, 32 is shown in FIG. 6 wherein each latch 28, 30, 32 is in the latched position corresponding to the respective shuttle 54 being in the actuated position as shown in FIG. 5. A reflection for each latch 28, 30, 32 is illustrated by first, second, and third crests 68, 70, 72. The first reflection is received by time domain reflectometer 42 at time $2T_1$ where $T_1$ is the propagation time required for the energy pulse to transmit from cable head 44 to conductor bend apparatus 52 associated with first latch 28. This reflection creates first crest 68 as shown in FIG. 6. Similarly, reflections received at times $2T_2$ and $2T_3$ correspond to unlatched second and third latches 30, 32, respectively and create second and third crests 70, 72.

A far end reflection received at time $2T_4$ occurs because of an impedance mismatch at cable tail 48 and creates a fourth crest 74. A near end reflection occurs because of an impedance mismatch at cable head 44 and creates fifth crest 75. Fourth and fifth crests 74, 75 are larger in magnitude than first, second, and third crests 68, 70, 72 because the reflection caused by an impedance mismatch is larger than the reflection caused by a bent cable region.

Microprocessor 50 receives the reflection data from time domain reflectometer 42 to determine the corresponding latch positions. For example, if microprocessor 50 detects any of first, second, or third crests 68, 70, 72, it knows that at least one of latches 28, 30, 32 is unlatched and disables mover 24 from rotating frame members 17, 19 and backboard 13. Thus, if microprocessor 50 detects that any of latches 28, 30, 32 are unlatched, backboard 13 will not be moved by mover 24.

Microprocessor 50 is also configured to detect the position specific to each respective latch 28, 30, 32. Microprocessor 50 is configured to measure the time delay between transmitting the energy pulse ($T_0$) and receiving each of the respective reflections. Microprocessor 50 then multiplies the time delay of the reflected portion of the energy pulse by the propagation speed of the energy pulse to determine the distance traveled by the reflected portion of the energy pulse. This distance is divided by two to determine the distance from time domain reflectometer 42 to the reflective region that generated the reflected portion of the energy pulse. Microprocessor 50 compares this distance with predetermined distances known for each latch 28, 30, 32 to determine which latch 28, 30, 32 is in the unlatched position.

Figure 7:
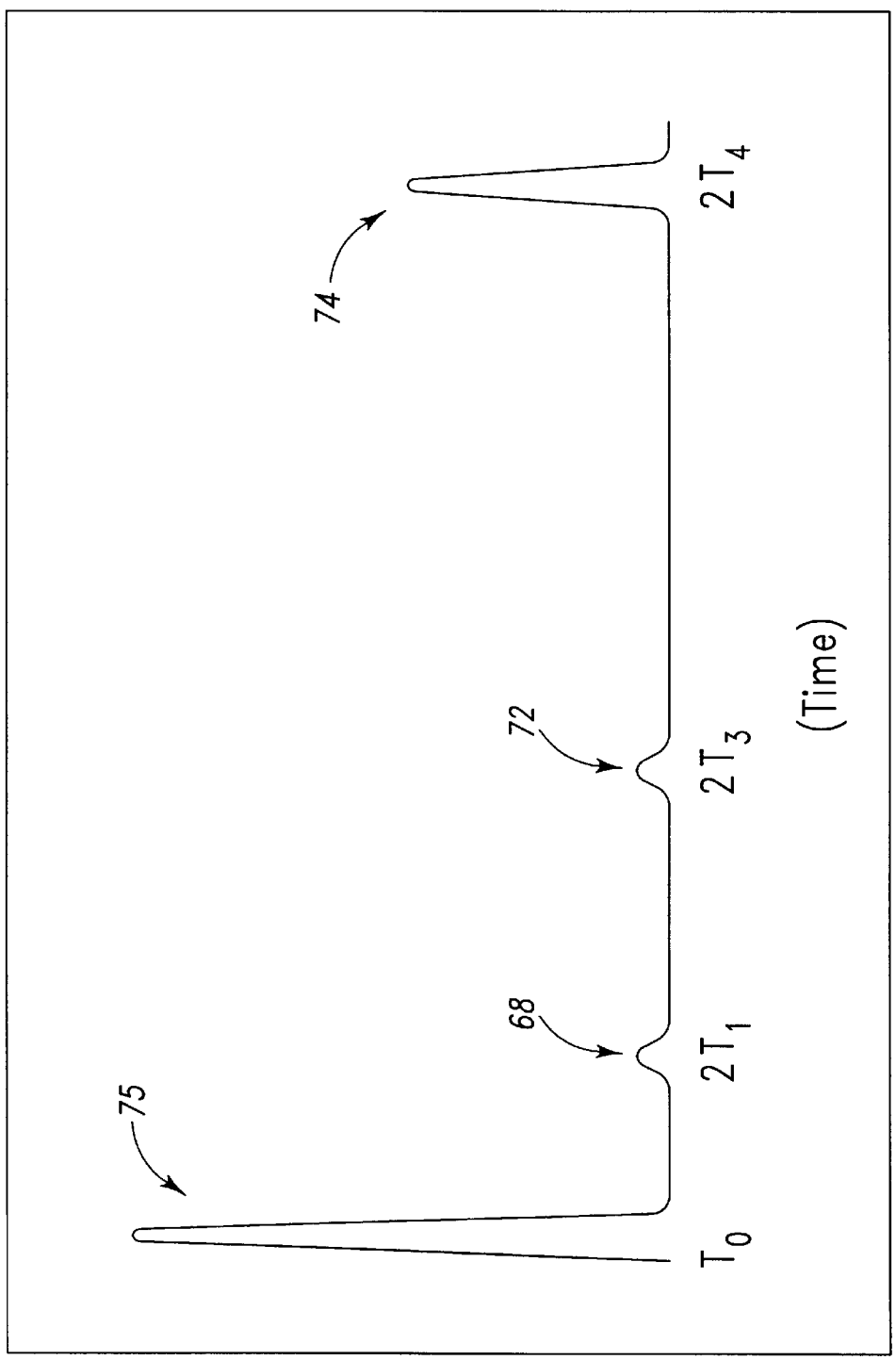
FIG. 7 is a graph similar to FIG. 6 showing a reading when the first and third latches are in the unlatched position and the second latch is in the latched position generating two corresponding medium crests between the large crests.

Another time domain reflectometer reading is shown in FIG. 7 wherein first and third latches 28, 32 are in the unlatched position and second latch 30 is in the latched position. In this situation, reflections are received at times $2T_1$ and $2T_3$ to create first and third crests 68, 72. Microprocessor 50 detects these crests 68, 72 and determines that first and third latches 28, 32 are unlatched and will not permit mover 24 to move frame members 17, 19 and backboard 13.

Figure 8:
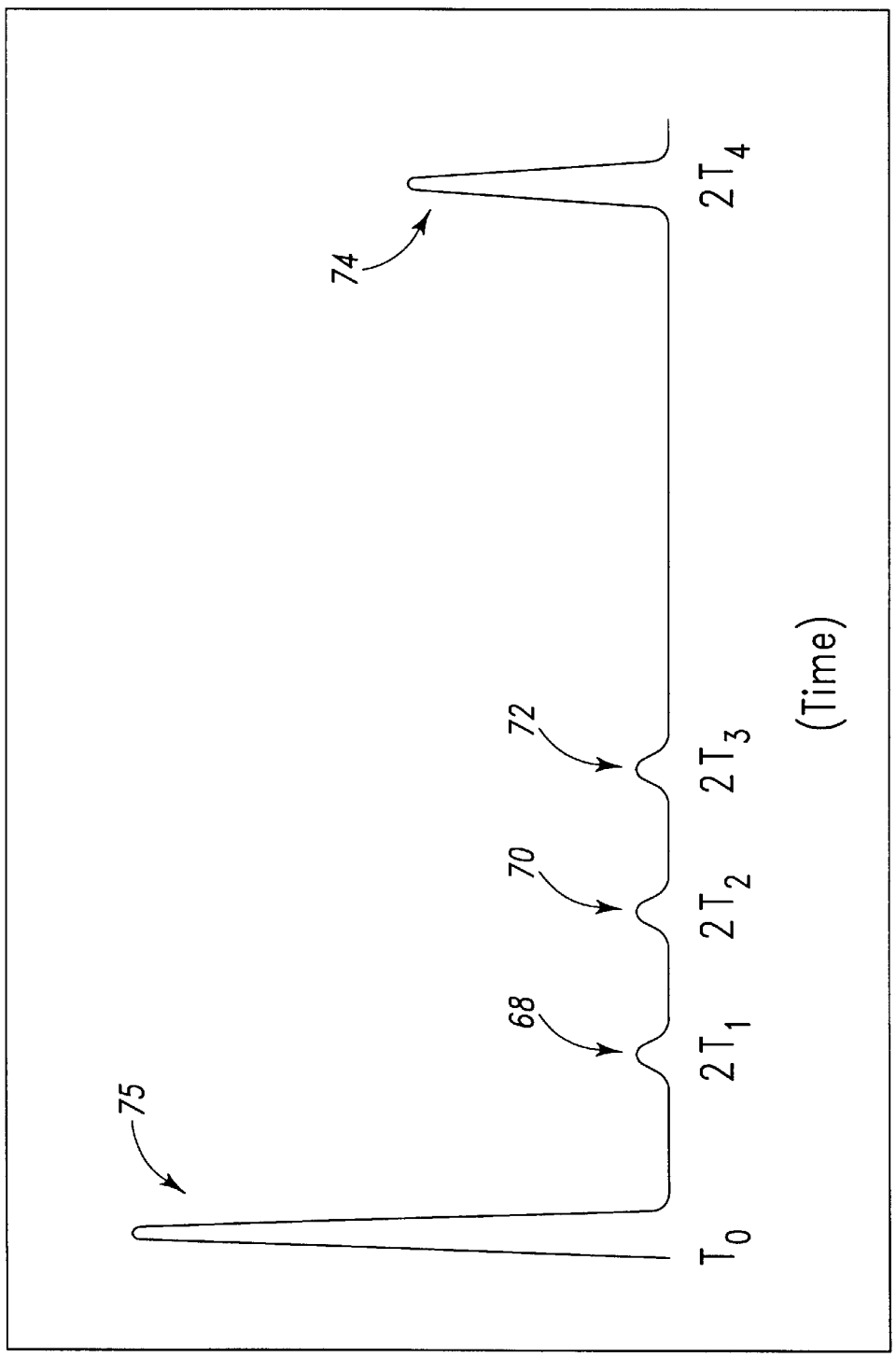
FIG. 8 is a graph similar to FIG. 6 showing a reading when the first and third latches are in the unlatched position and the second latch is in a partially latched position generating two corresponding medium crests and a small crest between the two medium crests.

Another time domain reflectometer reading is shown in FIG. 8 corresponding to first and third latches 28, 32 being in the unlatched position and second latch 30 being in a partially latched position. Microprocessor 50 detects each of resulting first, second, and third crests 68, 70, 72 to prevent movement of frame members 17, 19 and backboard 13. Microprocessor 50 also recognizes the reduced magnitude of second crest 70 as a latch that is only partially latched. Thus, microprocessor 50 detects the presence of any partially or fully unlatched positions of latches 28, 30, 32 to prevent rotation of frame members 17, 19 or backboard 13 unless each latch is completely latched to backboard 13.

Microprocessor 50 is also configured to detect failures in cable 34 due to extended use, breaks, kinks, fraying, or other defects in cable 34. Such failures create large impedance mismatches and a large reflection of a transmitted energy pulse. Microprocessor 50 is also configured to distinguish between such failures and the unlatched position of any of first, second, or third latches 28, 30, 32 by comparing either the magnitude or time delay of the reflection with predetermined values for the magnitudes and time delays expected for latches 28, 30, 32.

If a crest is detected by time domain reflectometer 42 having a time delay that does not match the predetermined time delay for latches 28, 30, 32, microprocessor 50 knows that the crest creating condition is not occurring in a region associated with latches 28, 30, 32. Microprocessor 50 then generates an error message if an energy pulse reflection is received at a time not corresponding to the location of a first, second, or third latches 28, 30, 32, cable head 44, or cable tail 48. For example, in FIG. 9, a crest 77 is generated because of a cable failure after third latch 32 at time $2T_F$. Because this crest 77 does not correspond to known crests 75, 68, 70, 72, 74 at respective times $T_0$, $2T_1$, $2T_2$, $2T_3$, and $2T_4$, microprocessor knows that a failure has occurred in cable 34.

If a failure occurs at any of conductor manipulators 29, time domain reflectometer 42 may obtain a false time delay reading mimicking a latch in the unlatched position. Thus, microprocessor 50 also compares the magnitude of the reflection with the predetermined magnitude associated with a bent region to determine whether the reflection is the result of an associated latch 28, 30, 32 being in the unlatched position or a failure that has occurred at the region associated with one of latches 28, 30, 32. Microprocessor 50 generates an error message if a pulse is received having a magnitude that does not correspond to the predetermined magnitude of first, second, or third latches 28, 30, 32 and cable tail 48.

Figure 10:
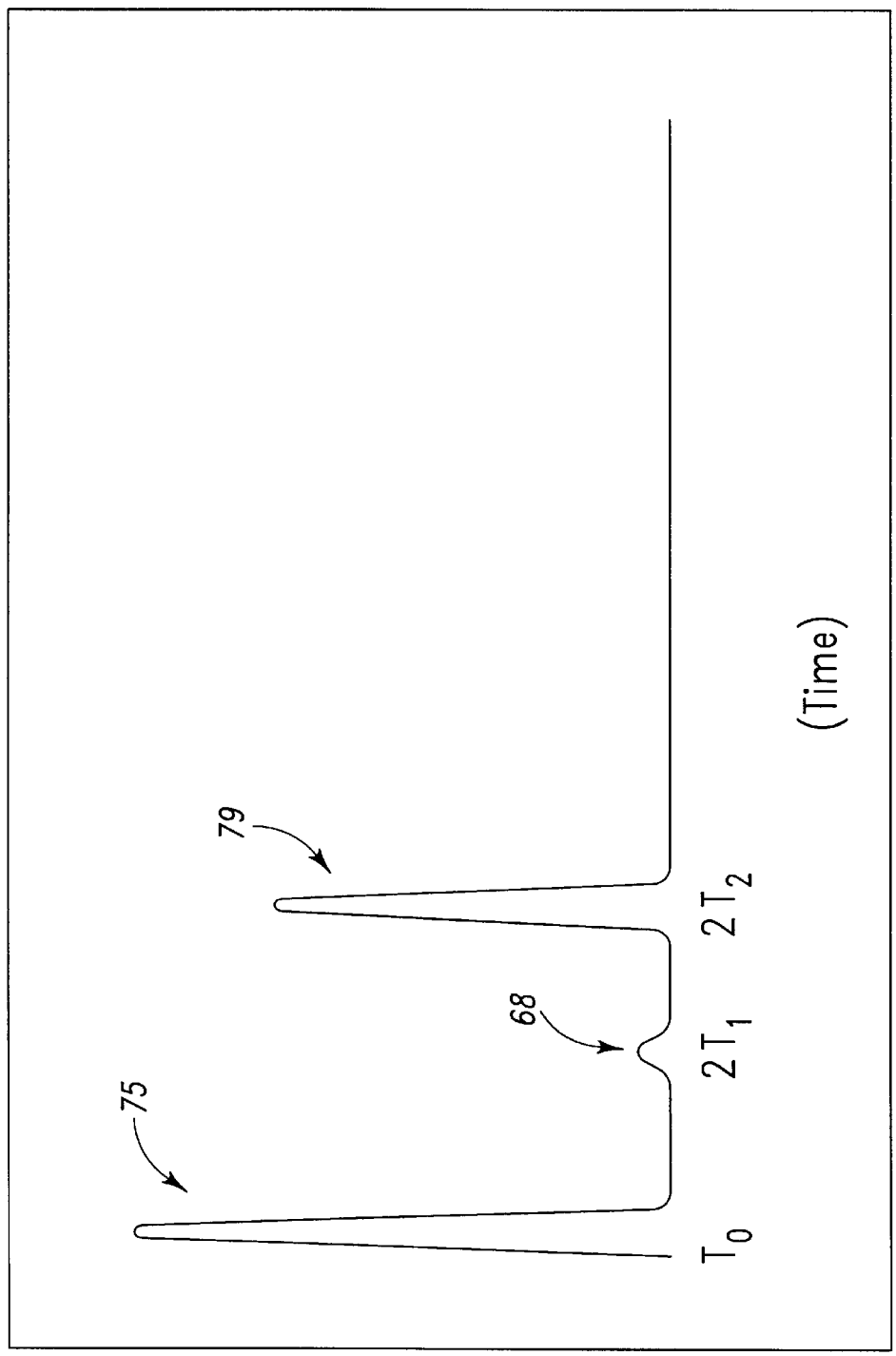
FIG. 10 is a graph similar to FIG. 6 showing a reading when a failure has occurred in the conductor at the second latch generating a large crest after the crest associated with the first latch.

For example, FIG. 10 shows a time domain reading for conductor 34 when (1) first latch 28 is in the unlatched position and (2) a cable failure has occurred at the cable region associated with second latch 30. This failure creates a crest 79 at time $2T_2$ that mimics the time delay of crest 70. Microprocessor 50 compares the magnitude of crest 79 with the known unlatched magnitude of crest 70 associated with second latch 30 and determines that a cable failure has occurred, not that second latch 30 is in the unlatched position.

Figure 9:
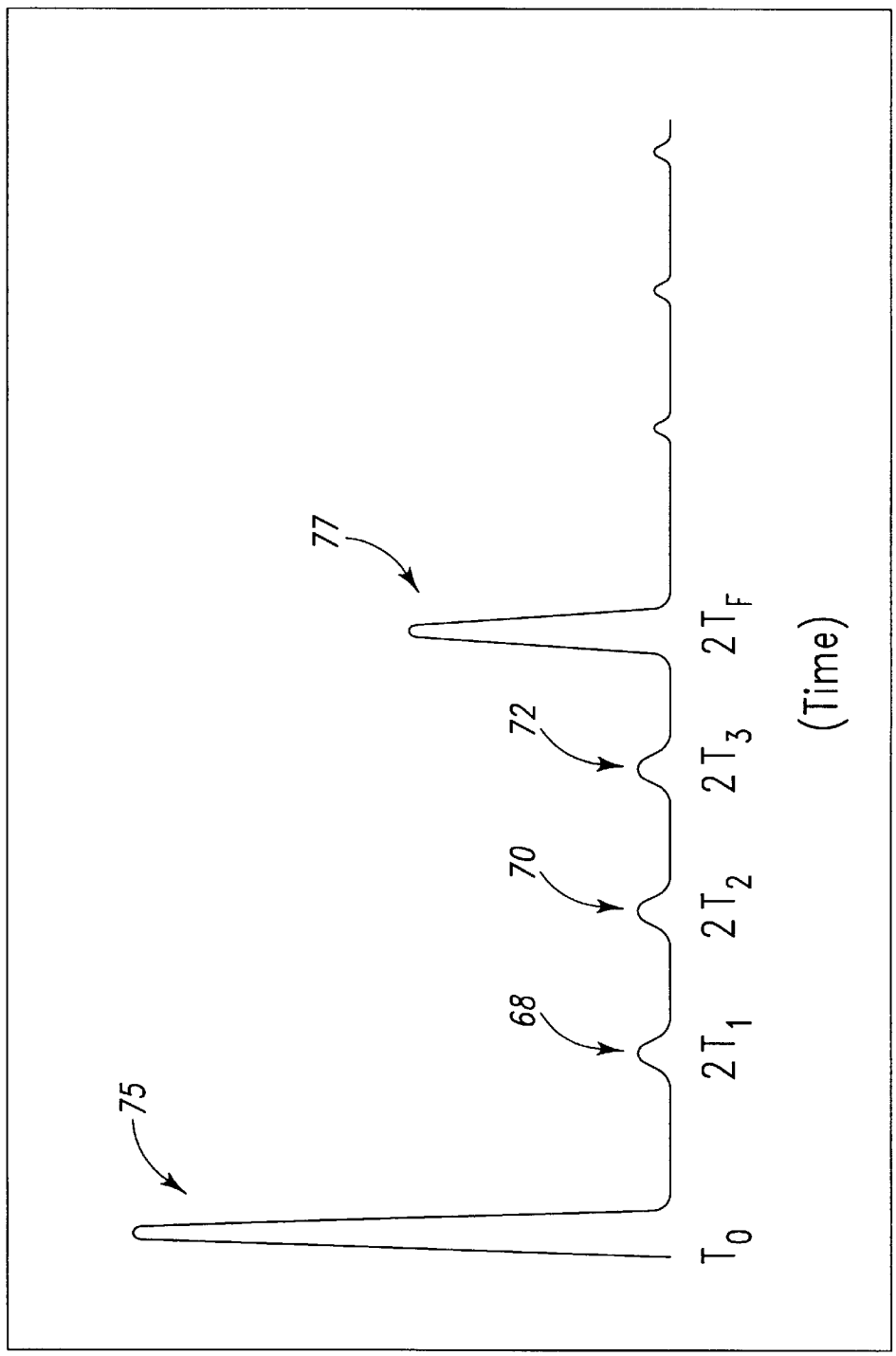
FIG. 9 is graph similar to FIG. 6 showing a reading when a failure has occurred in the conductor after the third latch generating a large crest after the three crests associated with the latches.
Figure 11:
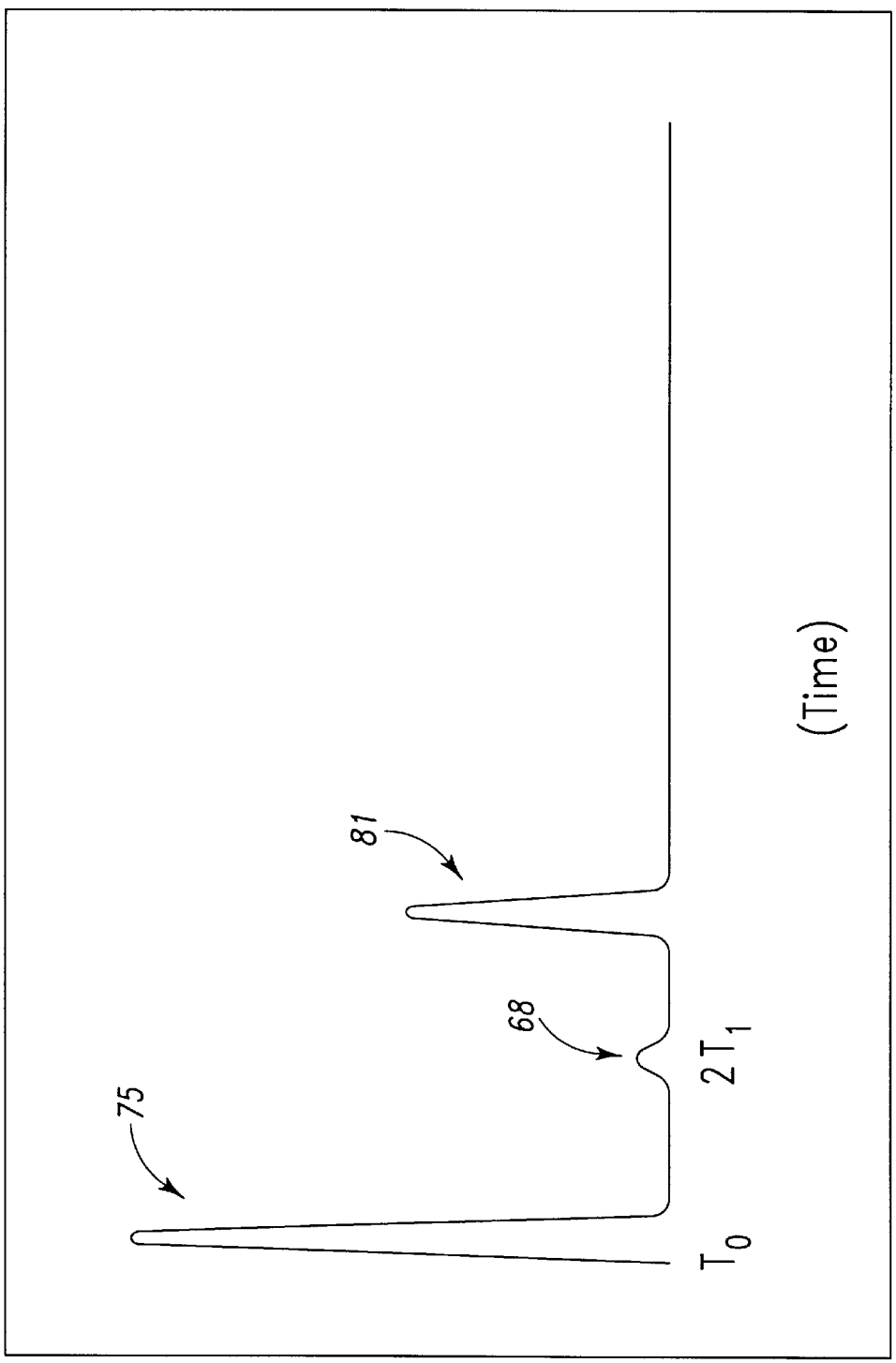
FIG. 11 is graph similar to FIG. 6 showing a reading when a failure has occurred in the conductor after the first latch generating a large crest after the crest associated with the first latch.

Cable failures can also prevent further propagation of the energy pulse through cable 34 so that time domain reflectometer 42 will not receive data for latches located farther down cable 34, and will therefore generate a potentially false reading indicating that the latches located farther down cable 34 are latched. FIGS. 9–11 are time domain reflectometer readings for failures in cable 34 at various locations. FIG. 9 illustrates a failure in cable 34 after all three latches 28, 30, 32 so that fourth crest 74 is not generated and returned to time domain reflectometer 42. FIG. 10 illustrates a failure in cable 34 within the region associated with conductor bend apparatus 40 corresponding to second latch 30. FIG. 11 illustrates a failure in cable 34 located prior to second latch 30 preventing time domain reflectometer 42 from obtaining data regarding the position of second and third latches 30, 32. These failures provide false crest 77, 79, 81 suggesting that first and second latches 28, 30 are in the unlatched position and third latch 34 is in the latched position. Also, if cable tail 48 is not properly terminated, a large impedance mismatch will occur and the time domain reflectometer 42 will receive a larger tail end reflection at cable head 44 at time $2T_4$.

To aid in preventing erroneous readings based on the absence of crests, microprocessor 50 receives reflection data from both time domain reflectometer 42 and power meter 46. Microprocessor 50 compares the reading received from power meter 46 with a predetermined value. If the reading is less than the predetermined value, microprocessor 50 knows that a cable failure has occurred because an unexpected portion of the energy pulse was either reflected or "leaked" do to a cable failure. Thus, microprocessor 50 generates an error message suggesting a failure in the cable if the reading from power meter 46 indicates an excessive attenuation of the energy pulse. Microprocessor 50 is also configured to detect the position of the failure based on the time delay reading of the respective false crest generated by the cable failure.

According to an alternative embodiment, the length of cable 34 is increased between each of conductor manipulators 29. Lengthening these sections of cable 34 increases the time in which the reflections return to time domain reflectometer 42. Increases in the reflection time reduce the necessary resolution of time domain reflectometer 42. For example, a 1 ft. resolution would require time domain reflectometer 42 to operate in the 1–2 GHz range. By coiling cable 34 between conductor manipulators 29, the speed of time domain reflectometer 42 may be decreased, thus lowering the overall cost of the system. Fiber optic cable is especially suitable for this, due to its flexibility and lack of crosstalk. Alternatively, this configuration may also be practiced with other cable types.

According to alternative embodiments, other cable types are used. For example, according to an alternative embodiment, an electrical cable, such as coaxial cable, is used. In a latch position detector using coaxial cable, shuttle 54 forces the conductors of the cable closer together when corresponding latches 28, 30, 32 are in the unlatched position to change the inductive property of the cable from a first state to a second state. This difference in the electrical quality of the coaxial cable is then detected to indicate that the respective latch is in the unlatched state.

According to another embodiment, a pneumatic conductor is used. As the respective latch or other bed component moves from one position to another, the property of the pneumatic conductor is altered. For example, a kink or other restriction is placed in the pneumatic conductor when the associated latch moves to an unlatched position. A sensor detects the change in the overall resistance of the pneumatic conductor to detect that one of the latches is in the unlatched position. Similarly, any other suitable energy pulse can be transmitted through a suitable conductor. For example, sound or electricity may be sent through a conductor to transmit a detectable change of state in the respective conductor. Such a change is then detected by a sensor to indicate the change in position of the respective bed component.

Although the invention has been described in detail with reference to certain illustrated embodiments, variations exist within the scope and spirit of the invention as described and as defined in the following claims.

What is claimed is:

1. A bed comprising
a support surface configured to support a person,
a bedframe configured to support the support surface, the bedframe including a first component and a second component configured to move relative to the first component between a first and a second position, and
a position detector including a conductor and a sensor, the conductor having a property changeable between first and second states, the second component of the bedframe being positioned to change the property of the conductor from the first state to the second state upon movement of the second component from the first position to the second position, the sensor being coupled to the conductor to detect the state of the property of the conductor to determine the position of the second component relative to the first component.

2. The bed of claim 1, wherein the conductor is a fiber optic cable.

3. The bed of claim 2, wherein the property is the shape of the fiber optic cable.

4. The bed of claim 3, wherein the conductor has a bend that has a first bend radius small enough to create a reflective region in the fiber optic cable when in the second state and the conductor has a second bend radius larger than the first bend radius when in the first state.

5. The bed of claim 2, wherein the sensor includes a time domain reflectometer configured to generate an energy pulse and to detect a portion of the energy pulse received from the fiber optic cable.

6. The bed of claim 5, wherein the sensor further includes a power meter coupled to the conductor to receive a portion of the energy pulse transmitted through the fiber optic cable.

7. The bed of claim 5, wherein the sensor further includes a microprocessor coupled to the time domain reflectometer to generate a component position signal indicative of the position of the second component relative to the first component.

8. The bed of claim 5, wherein the sensor further includes a microprocessor configured to detect a defect in the fiber optic cable by comparing an expected value of the portion of the energy pulse received from the conductor to an actual value based on the portion of the energy pulse received from the conductor.

9. The bed of claim 8, wherein the expected value is a predicted magnitude of the portion of the energy pulse and the actual value is the magnitude of the portion of the energy pulse received from the conductor.

10. The bed of claim 8, wherein the expected value is a predicted time delay of the portion of the energy pulse received from the conductor and the actual value is the actual time delay of the portion of the energy pulse from the conductor.

11. The bed of claim 8, wherein the sensor further includes a power meter coupled to the conductor to generate a power reading, the power meter is coupled to the microprocessor, the expected value is a predicted power reading from the power meter, the actual value is the power reading generated by the power meter, and the microprocessor is configured to generate an error message based on a comparison of the actual and expected values.

12. The bed of claim 1, wherein the conductor is a coaxial cable.

13. The bed of claim 12, wherein the property is the impedance of a region of the coaxial cable changed by the movement of the second frame component of the bedframe.

14. The bed of claim 1, wherein the position detector is configured to send a signal into the conductor and the sensor receives the signal from the conductor to determine the position of the second component based on the signal received from the conductor.

15. The bed of claim 14, wherein the signal is electromagnetic.

16. The bed of claim 14, wherein the signal is electric.

17. The bed of claim 14, wherein the signal is pneumatic.

18. The bed of claim 14, wherein the sensor is configured to generate an error message when a defect is detected in the conductor based on the signal received from the conductor.

19. The bed of claim 1, wherein the position detector further includes a contact element positioned between the second component and the conductor to transfer movement of the second component to the conductor.

20. The bed of claim 19, wherein the position detector further includes a conductor bend apparatus configured to cooperate with the contact element to bend the conductor as the second component moves between the first and second positions.

21. The bed of claim 20, wherein the conductor bend apparatus includes a first pulley and a second pulley and the contact element is positioned to move between a deactuated position and an actuated position pushing the conductor between the first and second pulleys to urge the conductor into a bent position.

22. The bed of claim 21, wherein the conductor bend apparatus further includes a spring coupled to the conductor to bias the conductor away from the bent position.

23. The bed of claim 1, wherein the first component of the bedframe is a frame member and the second component is a latch positioned to couple the support surface to the frame member when in the first position and to permit the support surface to be removed from the frame member when in the second position.

24. The bed of claim 23, wherein the bedframe further includes a mover coupled to the frame member, the mover is configured to move the frame member and the support surface, and the position detector is in communication with the mover to disable the mover from moving the frame member and the support surface when the position detector senses that the latch is in the second position.

25. A bed comprising a support surface configured to support a person, a bedframe configured to support the support surface, the bedframe including a frame member and multiple components configured to move relative to the frame member between first and second positions, and a position detector including a conductor and a sensor, each of the multiple components being positioned to communicate a change in position of said component to the conductor, the sensor being coupled to the conductor to detect the change in position of each of the multiple components to determine the positions of the components.

26. A bed comprising a support surface configured to support a person, a bedframe configured to support the support surface, the bedframe including a frame member and multiple components configured to move relative to the frame member between first and second positions, a position detector including a conductor and a sensor, each of the multiple components being positioned to communicate a change in position of said component to the conductor, the sensor being coupled to the conductor to detect the change in position of each of the multiple components to determine the positions of the components, and a board defining the support surface, the multiple components being latches positioned to move between the first position latching the board to the frame member and the second position permitting the board to be removed from the frame member.

27. The position detector of claim 26, wherein the bedframe further includes a mover coupled to the frame member and configured to move the frame member and the board and the sensor is coupled to the mover to disable movement of the mover if any of the latches are in the second position.

28. A bed comprising a support surface configured to support a person, a bedframe configured to support the support surface, the bedframe including a frame member and a latch configured to move relative to the frame member between a first position and a second position, the latch being further configured to couple the support surface to the frame member when in the first position and to permit the support surface to be removed from the frame member when in the second position, and a position detector including a conductor and a sensor, the conductor having a property changeable between first and second states, the latch of the bedframe being positioned to change the property of the conductor from the first state to the second state upon movement of the latch from the first position to the second position, the sensor being coupled to the conductor to detect the state of the property of the conductor to determine the position of the latch relative to the frame member.

29. The bed of claim 28, wherein the bedframe further includes a mover coupled to the frame member, the mover is configured to move the frame member and the support surface, and the position detector is in communication with the mover to disable the mover from moving the frame member and the support surface when the position detector senses that the latch is in the second position.

* * * * *